US011172692B2

(12) United States Patent
Harris et al.

(10) Patent No.: US 11,172,692 B2
(45) Date of Patent: Nov. 16, 2021

(54) HORSE SUPPLEMENT

(71) Applicant: Mars, Incorporated, McLean, VA (US)

(72) Inventors: Patricia Harris, Leicestershire (GB); Verity Beaton, Bedfordshire (GB); Clare Barfoot, Leicestershire (GB)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 16/780,964

(22) Filed: Feb. 4, 2020

(65) Prior Publication Data
US 2020/0236967 A1 Jul. 30, 2020

Related U.S. Application Data

(63) Continuation of application No. 16/026,747, filed on Jul. 3, 2018, now Pat. No. 10,588,332, which is a continuation of application No. 14/767,232, filed as application No. PCT/EP2014/052940 on Feb. 14, 2014, now Pat. No. 10,092,022.

(30) Foreign Application Priority Data

Feb. 15, 2013 (GB) ..................... 1302755

(51) Int. Cl.
*A61K 36/00* (2006.01)
*A23K 10/16* (2016.01)
*A23K 10/18* (2016.01)
*A23K 10/30* (2016.01)
*A23K 20/174* (2016.01)
*A23K 20/163* (2016.01)
*A23K 50/20* (2016.01)
*A61K 31/198* (2006.01)
*A61K 31/732* (2006.01)
*A61K 36/06* (2006.01)
*A61K 36/16* (2006.01)
*A61K 36/258* (2006.01)
*A23K 20/142* (2016.01)

(52) U.S. Cl.
CPC ............ *A23K 10/16* (2016.05); *A23K 10/18* (2016.05); *A23K 10/30* (2016.05); *A23K 20/142* (2016.05); *A23K 20/163* (2016.05); *A23K 20/174* (2016.05); *A23K 50/20* (2016.05); *A61K 31/198* (2013.01); *A61K 31/732* (2013.01); *A61K 36/06* (2013.01); *A61K 36/16* (2013.01); *A61K 36/258* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,268,384 A | 12/1993 | Galardy |
| 5,932,595 A | 8/1999 | Bender et al. |
| 5,932,763 A | 8/1999 | Scott et al. |
| 5,968,795 A | 10/1999 | Dixon et al. |
| 6,080,410 A | 6/2000 | Bewicke |
| 6,288,063 B1 | 9/2001 | Kluender et al. |
| 6,902,739 B2 | 6/2005 | McPeak et al. |
| 6,911,449 B2 | 6/2005 | VanZandt et al. |
| 6,924,273 B2 | 8/2005 | Pierce |
| 7,232,585 B2 | 6/2007 | Quan et al. |
| 7,601,373 B2 | 10/2009 | McCormick |
| 8,470,876 B2 | 6/2013 | Bruheim et al. |
| 8,501,218 B2 | 8/2013 | Hurwitz |
| 8,633,246 B2 | 1/2014 | Fritsch et al. |
| 2002/0068718 A1 | 6/2002 | Pierce |
| 2002/0197289 A1 | 12/2002 | Chevalier et al. |
| 2004/0115309 A1 | 6/2004 | Harris |
| 2004/0242503 A1 | 12/2004 | Silva |
| 2005/0043405 A1 | 2/2005 | Fritsch et al. |
| 2005/0158406 A1 | 7/2005 | McPeak et al. |
| 2006/0222699 A1 | 10/2006 | Gilinski |
| 2007/0155666 A1 | 7/2007 | Alkayali et al. |
| 2007/0231377 A1 | 10/2007 | Abou-Nemeh |
| 2008/0233245 A1 | 9/2008 | White et al. |
| 2008/0305096 A1 | 12/2008 | Verdegem et al. |
| 2009/0232853 A1 | 9/2009 | Harris |
| 2010/0196352 A1 | 8/2010 | O'Donovan et al. |
| 2010/0291053 A1 | 11/2010 | Clayton et al. |
| 2011/0091522 A1 | 4/2011 | Murwitz |
| 2011/0206721 A1 | 8/2011 | Nair |
| 2011/0262595 A1 | 10/2011 | Lee |
| 2012/0121754 A1 | 5/2012 | Green |
| 2012/0129785 A1 | 5/2012 | Fleuranges et al. |

(Continued)

FOREIGN PATENT DOCUMENTS

| | | | |
|---|---|---|---|
| DE | 102011008478 A1 | 8/2011 | |
| DE | 102011006535 A1 | 10/2012 | |

(Continued)

OTHER PUBLICATIONS

Anonymous, Equine Solutions Catalog: Relaxing supplements—Equilite relax blend, Retrieved from the Internet: URL:http//web.archive.org/web/20121214024614/http://www.myfineequine.com/relax1.htm, Dec. 14, 2012, 6 pgs.

(Continued)

*Primary Examiner* — Qiuwen Mi

(74) *Attorney, Agent, or Firm* — Morrison & Foerster LLP

(57) ABSTRACT

The present invention relates to compositions and their uses, specifically provides supplements for equines, in particular horses and ponies. Such a composition is ideal for horses and ponies where promoting, supporting or maintaining calm behavior is desired or required.

9 Claims, 6 Drawing Sheets

(56) References Cited

U.S. PATENT DOCUMENTS

| | | |
|---|---|---|
| 2012/0197067 A1 | 8/2012 | Kat et al. |
| 2012/0231087 A1 | 9/2012 | Bruheim et al. |
| 2012/0301546 A1 | 11/2012 | Hassan |
| 2013/0017182 A1 | 1/2013 | Lukina |
| 2013/0034530 A1 | 2/2013 | Fantz |
| 2013/0344010 A1 | 12/2013 | Pompejus |
| 2015/0374013 A1 | 12/2015 | Harris et al. |
| 2018/0317521 A1 | 11/2018 | Harris et al. |

FOREIGN PATENT DOCUMENTS

| | | | |
|---|---|---|---|
| EP | 2481300 A1 | 8/2012 | |
| FR | 2949646 B1 | 1/2012 | |
| GB | 2385768 B | 6/2005 | |
| GB | 2424370 A | 9/2006 | |
| JP | 2013169153 A | 9/2013 | |
| WO | 02/24002 A2 | 3/2002 | |
| WO | 03/061401 A2 | 7/2003 | |
| WO | 2004/112776 A2 | 12/2004 | |
| WO | 2005079764 A1 | 9/2005 | |
| WO | 2008/115563 A1 | 9/2008 | |
| WO | 2008/135960 A2 | 11/2008 | |
| WO | 2010/067206 A1 | 6/2010 | |
| WO | 2011/011472 A1 | 1/2011 | |
| WO | 2012/100991 A1 | 8/2012 | |
| WO | 2013149323 A1 | 10/2013 | |

OTHER PUBLICATIONS

Anonymous, Placid, Retrieved from the Internet: URL:http//web.archive.org/web/20130129091749/http://www.dodsonandhorrell.com/our-feeds/herbs-supplements/behave/placid.htm, Apr. 22, 2012, 3 pgs.

Bailey et al., Identification of Equine Cecal Bacteria Producing Amines in an In Vitro Model of Carbohydrate Overload, Applied and Environmental Microbiology, vol. 69, No. 4, pp. 2087-2093 (Apr. 2003).

Bailey et al., Plasma 5-hydroxytryptamine Constricts Equine Digital Blood Vessels in Vitro: Implications or Pathogenesis of Acute Laminitis, Equine Veterinary Journal, vol. 30, No. 2, pp. 124-130 (Mar. 1998).

Bailey et al., Production of Amines in Equine Cecal Contents in an In Vitro Model of Carbohydrate Overload, Journal of Animal Science, vol. 80, No. 10, pp. 2656-2662 (Oct. 2002).

Eustace, Equine Laminitis, The Laminitis Trust, Retrieved from the Internet: URL:http://www.laminitis.org/>, 18 pages, Mar. 15, 2005.

Harris, Nutrition, behavior and the role of supplements for calming horses: The veterinarian's dilemma, Veterinary Journal, vol. 170, No. 1, pp. 10-11, (2005).

Hoffman et al., Hydrolyzable Carbohydrates in Pasture, Hay, and Horse Feeds: Direct Assay and Seasonal Variation, Journal of Animal Science, vol. 79, No. 2, pp. 500-506 (Feb. 2001).

Johnson et al., Activation of Extracellular Matrix Metalloproteinases in Equine Laminitis, The Veterinary Record, vol. 142, No. 15, pp. 392-396 (Apr. 11, 1998).

Jones et al., Nutraceuticals for equine practice, Journal of Equine Veterinary Science, Jones, Wildomar, CA, US, vol. 17(11), pp. 562-563 (1997).

Pollitt, et al., Batimastat (BB-94) Inhibits Matrix Metalloproteinases of Equine Laminitis, Equine Veterinary Journal, Supplement., No. 26, pp. 119-124 (Sep. 1998).

Russo, et al., Pharmaco-toxicological aspects of herbal drugs used in domestic animals, Natural Product Communications, vol. 4, No. 12, pp. 1777-1784 (2009).

Williams et al., Some commonly fed herbs and other functional foods in equine nutrition: A review, Veterinary Journal, vol. 178, No. 1, pp. 21-31 (2008).

Winther, et al., Does Litovet, A Herbal Remedy Made from Rosa Canina, Act as an Anti-Flammatory Agent in Horses Exposed to Strenuous Exercise—a Randomized, Placebo-Controlled, Parallel, Double-Blinded Study on the Immune System of Horses, Their Working Capacity and Behaviour, Osteoarthritis and Cartilage, vol. 16, Suppl. 4, p. S44 (Sep. 2008).

Calm Mix, A natural horse calming supplement with 5-HTP, chamomile and a soothing blend of herbs, The Herbal Horse, Retrieved online: https://www.horseandpethealth.com/natural-supplements-for-horses/calm-mlx/ 2009, 14 pages.

International Search Report and Written Opinion date Apr. 24, 2014, directed to International Application No. PCT/EP2014/052940; 10 pages.

International Search Report and Written Opinion dated Jul. 17, 2014, directed to International Application No. PCT/EP2014/052949; 9 pages.

Search Report dated Feb. 26, 2019, directed to EP Application No. 18201943.0; 8 pages.

HORSE SUPPLEMENT

CROSS-REFERENCE TO RELATED APPLICATIONS

This application is a continuation of U.S. application Ser. No. 16/026,747, filed on Jul. 3, 2018, which is a continuation of U.S. application Ser. No. 14/767,232, filed on Aug. 11, 2015, which issued as U.S. Pat. No. 10,092,022 on Oct. 9, 2018, and which is a 35 U.S.C. 371 of International Application No. PCT/EP2014/052940, filed on Feb. 14, 2014, which claims priority to GB Patent Application No. 1302755.2 filed on Feb. 15, 2013, the entirety of each of which is hereby incorporated herein by reference for any and all purposes.

FIELD

The present invention relates to compositions and their uses.

BACKGROUND

Equine animal supplementation can be taken to include products that 1) restore nutritional balance to a ration e.g. forage or cereal balancer feeds or 2) provide a safety margin when the nutrient quality of a ration is not known or 3) support animals to maintain health especially at times when they are at increased risk of certain conditions or 4) provide support when certain health problems are present. Supplementation includes compounds or plant material that are used to provide one or more nutrients in a specific preparation or one or more non-nutritional factors in order to support metabolic process or provide some other purported benefit.

SUMMARY

The present invention provides supplements for equines, in particular horses and ponies.

According to a first aspect of the invention (also referred to as Energy Boost), there is provided a composition comprising two or more of the following three energy sources: 1) a source of rapidly available carbohydrate; 2) a source of more complex but rapidly digestible and moderately quickly available carbohydrate and 3) branched chain amino acids, together with Ginkgo, Ginseng root and optionally a source of B vitamins (e.g. yeast). Sources of the rapidly available carbohydrate (sugar) include mono or di-saccharides, glucose, sucrose, dextrose and fructose. Sources of the moderately quickly available carbohydrate include pectin, such as apple, pear, and other citrus fruits, as well as sugar beet and other feeds high in non-starch polysaccharides. Sources of B vitamins include synthetic B vitamins, flours and other foods enriched with B vitamins, root vegetables, molasses, baker's yeast and yeast, including Saccharomyces cerevisiae. Sources of yeast to provide the B vitamins include fermented products, vinegar and the many foods that it is contained in, such as soy sauce, mushrooms.

Such a composition is ideal for horses and ponies where encouraging a more energetic performance is required. The composition encourages a more energetic performance without feeding unnecessary starch based feeds which may provide unwanted calories. The composition contains rapid and moderately available carbohydrate sources and optionally branched chain amino acids to help provide a mixed energy profile. It includes: ginseng and gingko which have been traditionally used to support mental capacity and are both known as "feel good" herbs. Branched chain amino acids provide additional support to an energetic performance. A rich source of B vitamins are optionally included which are involved in energy metabolism.

Any one or more of the ingredients may be present in the following ranges (to provide the component of which they are a source): source to provide rapidly available sugar (e.g. glucose) at 5-100 g, source to provide moderately available carbohydrate (e.g. pectin) at 2-50 g, source to provide gingko (leaf) at 1-10 g, source to provide ginseng root at 1-10 g, source to provide branched amino acids at 2-15 g, source to provide B vitamins (e.g. providing a source which is yeast at 2-20 g).

The composition may comprise glucose, apple pectin, gingko leaf, ginseng root (may be Siberian), leucine, valine, isoleucine and yeast.

The composition may comprise the following: glucose or dextrose about 24 g; apple pectin about 5 g; ginkgo leaf about 2 g; ginseng root about 5 g; leucine about 3.75 g; valine about 1.9 g; isoleucine about 1.9 g; yeast about 5 g.

The composition may contain other ingredients which are used in an equine food, such as binders, flavorants (e.g. spearmint flavor, rosemary extract), or carriers such as calcium carbonate, wheat feed and/or rapeseed oil or others such as oils, pharmaceutically acceptable excipient, stabilizing agents, anticaking agents, emulsifiers. Spearmint flavor can be included in the range of 1-1000 mg, e.g. 100 mg. Rosemary extract, a natural antioxidant, can be included in the range of 5-100 mg (e.g. 25 mg). Calcium carbonate can be included at a range of from 50 mg to 50 g (e.g. 12 g). Wheat feed can be included at a range from 100 mg to 30 g (e.g. 254 mg). Rapeseed oil can be included at a range of from 150 mg to 150 g (e.g. 250 mg) or milliliter equivalents.

The composition may be in the form of a food, such as a food supplement. The composition may be presented as a powder or crumbs, including a white powder or solid form. A powder is useful to sprinkle on the main food of the equine animal. Other forms include solid pellets, granules, tablets or a liquid.

The composition is recommended for feeding at the stated levels in a daily dose for a horse of 350-650 kg. A horse or pony of <350 kg would have a proportionally lower dose, adjusted accordingly. A horse of >650 kg would have a proportionally higher dose, adjusted accordingly.

The composition of the first aspect of the invention is particularly for use as an energy boost in equine animals. Energy boost includes a more energetic performance, a more focused performance and/or the horse being more alert. These include a decrease in reluctance behavior, less resistance/reluctance to go forward, increased trainability, less refusal at jumps, less lazy, less laid back.

The invention also relates to the use of the composition of the first aspect may be as an energy boost in equine animals.

The invention also relates to a method of boosting energy in an equine, comprising administering, to an equine, a composition according to the first aspect of the invention.

The invention also provides a method of making a composition, as claimed in the first aspect of the invention, comprising mixing together the ingredients into a composition e.g. in a tote tumbler to produce a powder, pellet or a paste.

According to a second aspect of the invention (also referred to as Challenged Skin and Coat) there is provided a composition comprising a source of vitamin C, a source of zinc, a source of biotin, a source of omega 3 fatty acid (e.g. linseed) and one or more of: any species of chamomile, any species of divers, any species of nettle, with optionally with a rich source of DHA, a source of supportive amino acids, such as methionine and arginine and optionally with yeast. A rich source of DHA can be any source of DHA (preferably a rich source).

Sources of vitamin C include sodium ascorbyl phosphate, ascorbic acid, orange, guava, red sweet pepper, kiwi and other fruit and vegetables. Sources of zinc include zinc oxide and grains. Sources of omega 3 fatty acid include fish, fish oils and vegetables including linseed. Sources of linseed include micronized linseed and linseed oil. A source of yeast includes those described above for the first aspect of the invention. Sources of the supportive amino acids include synthetic, extracted, as well as feeds rich in the particular amino acid. Source to provide biotin includes Saskatoon berries, Swiss chard, synthetic biotin.

This composition is ideal for feeding to all horses and ponies with poor coat condition, challenged skin health or sensitivity. The omega fatty acids may help support healthy skin and promote a shiny coat. It may also be beneficial in animals with fly bite sensitivity. It preferably includes a vegetable source of docosahexanoic acid (DHA) which is a potent omega 3 fatty acid. It contains a high level of biotin known to be important in skin health and hair growth and contains zinc which may support hair growth in some horses and ponies. It also includes: vitamin C, which has many important roles including acting as an anti-oxidant, collagen formation and is generally important in skin health; key supportive amino acids, such as methionine, a sulphur containing amino acid (sulphur is a building block of keratin—a key structural protein which makes up skin and hair) and arginine to support skin health and healing; and one or more of chamomile, divers and nettle, which are all traditionally used to support skin health. The composition can also be used to help maintain skin and coat health.

Any one or more of the ingredients may be present in the following ranges (to provide the component of which they are a source): source to provide vitamin C (e.g. vitamin C) at 0.25-10 g, source to provide zinc at 50-350 mg, source to provide biotin at 1-100 mg, a rich source to provide DHA at 50-300 mg (e.g. dried algae), source to provide methionine at 1-6 g, source to provide arginine at 0.5-5 g, source to provide omega 3 fatty acid (e.g. linseed) at 10-1000 g or milliliter equivalents of the oil, source to provide chamomile at 1-10 g, source to provide divers at 2-20 g, source to provide nettle at 2-20 g, source of yeast to provide 1-20 g of yeast.

The composition may comprise vitamin C, zinc, biotin, omega 3, fatty acid, with one or more of chamomile, clovers and nettle and optionally with one or more of methionine, arginine, a rich source of DHA and yeast.

The composition may comprise the following: Vitamin C about 1 g; zinc about 200 mg; biotin about 20 mg; linseed about 40.5 g; with one or more of the following chamomile about 3 g; divers about 10 g; nettle about 5 g and optionally one or more of methionine about 3 g; arginine about 1 g; yeast about 5 g omega 3 fatty acid (DHA) about 180 mg.

The composition may contain other ingredients which are used in an equine food, such as binders, flavorants (e.g. spearmint flavor, rosemary extract), or carriers such as calcium carbonate, wheat feed and/or rapeseed oil or others such as oils, pharmaceutically acceptable excipient, stabilizing agents, anticaking agents, emulsifiers. Spearmint flavor can be included in the range of 1-1000 mg, e.g. 100 mg. Rosemary extract, a natural antioxidant, can be included in the range of 5-100 mg (e.g. 25 mg). Calcium carbonate can be included at a range of from 50 mg-50 g (e.g. 12 g). Wheat feed can be included at a range from 100 mg to 30 g (e.g. 254 mg). Rapeseed oil can be included at a range of from 150 mg-150 g (e.g. 250 mg) or milliliter equivalents.

The composition may be in the form of a food, such as a food supplement. The composition may be presented as a powder or crumb or solid form. A powder is useful to sprinkle on the main food of the equine. Other forms include solid pellets, granules, tablets or a liquid.

The composition is recommended for feeding at the stated levels in a daily dose for a horse of 350-650 kg. A horse or pony of <350 kg would have a proportionally lower dose, adjusted accordingly. A horse of >650 kg would have a proportionally higher dose, adjusted accordingly.

The composition of the second aspect of the invention is particularly for use in supporting a healthy skin at times of increased risk of damage, infection, irritation, fly bites etc., or helping to support animals where the health of the skin has been compromised or they are prone to adverse skin conditions. It may also help to support an improvement the skin and/or coat condition of an equine. Such a use includes an improvement in coat shine, coat condition (more glossy, a sheen or gleam less dull) and an improvement in coat scurf.

The invention also relates to the use of the composition of the second aspect, for maintaining and/or improving the skin and/or coat condition of an equine.

The invention also relates to a method of maintaining and/or improving the skin and/or coat of an equine comprising administering, to an equine, a composition according to the second aspect of the invention.

The invention also provides a method of making a composition, according to the second aspect of the invention, comprising mixing together the ingredients into a composition e.g. in a tote tumbler to provide a powder, pellet or a paste.

A third aspect of the invention (also referred to as Calm Behavior), there is provided a composition comprising one or more sources of magnesium and any species of chamomile, with one or more of: any species of passion flower, any species of lemon balm or any species of hops, and optionally one or more of the B vitamins: thiamine, pyridoxine and folic acid and optionally yeast.

Sources of magnesium include magnesium oxide, magnesium aspartate hydrochloride, magnesium carbonate. Sources of yeast include those discussed above in relation to the first aspect of the invention.

The composition is ideal for horses and ponies to help promote calm and positive behavior. It preferably contains two sources of magnesium to help maximize absorption and effectiveness. The composition includes chamomile which has been traditionally fed to horses and has been shown to have a calming effect in other animals. The composition may additionally support hind gut health 1) by reducing the activity in the hind gut through the addition of yeast and the buffering effect of magnesium oxide and 2) the soothing action of chamomile. Acidity in the gut may be associated with behavioral issues in horses. It also contains one or more of hops, passiflora and lemon balm which are traditionally known as calming herbs. It preferably contains specific B vitamins such as thiamine, as well as a rich source of all B vitamins such as yeast, to help support the central nervous system.

Any one or more of the ingredients may be present in the following ranges: sources to provide magnesium at 2-15 g, source to provide thiamine at 50-500 mg, source to provide pyridoxine at 50-250 mg, source to provide folic acid at 2-100 mg, source to provide chamomile at 2-15 g, source to provide passion flower at 2-15 g, source to provide lemon balm at 2-15 g, source to provide hops at 2-15 g, source to provide yeast at 2-15 g.

The composition may comprise magnesium, chamomile, with one or more of passiflora incarnate, lemon balm, hops and optionally with one or more of yeast, thiamine, pyridoxine and folic acid.

The composition may comprise the following: magnesium about 6 g; thiamine about 250 mg; pyridoxine about 120 mg; folic acid about 20 mg; chamomile about 10 g; passiflora incarnate about 5 g; lemon balm about 3 g; hops about 3 g; yeast about 8 g.

The composition may contain other ingredients which are used in an equine food, such as binders, flavorants (e.g. spearmint flavor, rosemary extract), or carriers such as calcium carbonate, wheat feed and/or rapeseed oil or others such as oils, pharmaceutically acceptable excipient, stabilizing agents, anticaking agents, emulsifiers. Spearmint flavor can be included in the range of 1-1000 mg, e.g. 100 mg. Rosemary extract, a natural antioxidant, can be included in the range of 5-100 mg (e.g. 25 mg). Calcium carbonate can be included at a range of from 50 mg-50 g (e.g. 12 g). Wheat feed can be included at a range from 100 mg-30 g (e.g. 254 mg). Rapeseed oil can be included at a range of from 150 mg-150 g (e.g. 250 mg) or milliliter equivalents.

The composition may be in the form of a food, such as a food supplement. The composition may be presented as a powder or crumb or solid form. A powder is useful to sprinkle on the main food of the equine animal. Other forms include solid pellets, granules, tablets or a liquid.

The composition is recommended for feeding at the stated levels in a daily dose for a horse of 400-650 kg. A horse or pony of <400 kg would have a proportionally lower dose, adjusted accordingly. A horse of >650 kg would have a proportionally higher dose, adjusted accordingly.

The composition of the third aspect of the invention is particularly for use in promoting, supporting and maintaining calm behavior in an equine. Promoting calm behavior includes reduction in agitation or excitability, decrease in reluctant behavior (such as napping, refusals, fizziness, nervous behavior, spookiness or highly strung behavior).

The invention also relates to the use of the composition of the third aspect of the invention in promoting calm behavior in an equine.

The invention also relates to a method of promoting calm behavior in an equine comprising administering, to an equine, a composition according to the third aspect of the invention.

The invention also provides a method of making a composition, according to the third aspect of the invention, comprising mixing together the ingredients into a composition e.g. in a tote tumbler to provide a powder, pellet or a paste.

According to a fourth aspect of the invention (also referred to as Challenged Muscles), there is provided a composition comprising one or more of the key antioxidants of vitamin E, a source of vitamin C and selenium; two or more of the following key amino acids: lysine, methionine, threonine; a source of mixed branched chain amino acids; a source (preferably concentrated) of natural antioxidants, e.g. grape seed concentrate; a source of globular proteins such as beta-lactoglobulin, alpha lactoglobulin and serum albumin, e.g. whey protein; and optionally including arginine and optionally glutamine (or a glutamine rich source).

Sources of vitamin C include sodium ascorbyl phosphate, ascorbic acid. Sources of a mix of branched chain amino acids include amino acid supplements. The branched chain amino acids include leucine, valine, isoleucine. Sources of selenium include sodium selenite, Brazil nuts, sunflower seeds, bran. Concentrated sources of natural antioxidants include grape seed concentrate and the seeds of grapes. Sources of glutamine include extracted glutamine plus glutamine rich feeds and extracts such as wheat hydrolysates, glutamine dipeptides.

The composition is ideal for active horses and ponies or where muscle health is a concern. High levels of preferably more than one of the key antioxidants vitamin E, selenium and vitamin C are included to maximize absorption and efficiency (vitamin E and selenium are especially important in maintaining healthy muscles and are supported by vitamin C) as well as sources of natural antioxidants e.g. from grape seeds to support the body's natural anti-oxidant system. Whey protein may help support muscle and topline development. The composition contains a rich protein formula comprising one or more of the essential amino acids lysine, methionine and threonine which are important components of muscle. It also contains branched amino acids which can be used as a source of energy and may be especially important during the recovery from exercise. It preferably includes arginine which is one of the most utilized amino acids by the horse following exercise and glutamine, which is important in muscle health and may need to be supplemented in the diet of hard working horses.

Any one or more of the ingredients may be present in the following ranges: source to provide vitamin E at 5-2000 IU, a source to provide vitamin C at 0.5-10 g, source to provide lysine at 2-10 g, source to provide methionine at 1-6 g, source to provide threonine at 1-6 g, source to provide any mix of branched chain amino acids at 5-25 g, source to provide arginine at 0.5-3 g, a source to provide glutamine at 1-10 g optionally at 50 µg-50 g, a source to provide selenium at 0.1-1 mg, a source to provide natural antioxidants, e.g. grape seed concentrate at 0.25-5 g, a source to provide the globular proteins e.g. whey protein at 2-15 g.

The composition may comprise vitamin E, vitamin C, lysine, methionine, threonine, mix of branched chain amino acids, arginine, optionally glutamine, selenium, grape seed concentrate and whey protein.

The composition may comprise the following: vitamin E about 1000 IU; vitamin C about 750 mg; lysine about 7.5 g; methionine about 3 g; threonine about 1.5 g; leucine about 8 g; selenium about 0.4 g; grape seed concentrate about 0.5 g; whey protein about 11 g; valine about 3 g; isoleucine about 3 g; arginine about 1 g; glutamine about 6 g.

The composition may contain other ingredients which are used in an equine food, such as binders, flavorants (e.g. spearmint flavor, rosemary extract), or carriers such as calcium carbonate, wheat feed and/or rapeseed oil or others such as oils, pharmaceutically acceptable excipient, stabilizing agents, anticaking agents, emulsifiers. Spearmint flavor can be included in the range of 1-1000 mg, e.g. 100 mg. Rosemary extract, a natural antioxidant, can be included in the range of 5-100 mg (e.g. 25 mg). Calcium carbonate can be included at a range of from 50 mg-50 g (e.g. 12 g). Wheat feed can be included at a range from 100 mg-30 g (e.g. 254 mg). Rapeseed oil can be included at a range of form 150 mg-150 g (e.g. 250 mg) or milliliter equivalents.

The composition may be in the form of a food, such as a food supplement. The composition may be presented as a powder or crumbs or solid form. A powder is useful to sprinkle on the main food of the equine animal. Other forms include solid pellets, granules, tablets or a liquid.

The composition is recommended for feeding at the stated levels in a daily dose for a horse of 350-650 kg. A horse or pony of <350 kg would have a proportionally lower dose, adjusted accordingly. A horse of >650 kg would have a proportionally higher dose, adjusted accordingly.

The composition of the fourth aspect of the invention is particularly for use in maintaining, supporting and/or improving muscle health in an equine, especially during periods of increased risk of muscle problems, e.g. when in high intensity work, when first start work/change the nature of any work, as well as those prone to muscle problems. Improving muscle health includes supporting the recovery of muscle after exercise in fit and unfit animals, supporting the recovery rate after any but especially high intensity exercise, soothing/easing stiffness after any but especially high intensity exercise, supporting the development of topline/muscle tone; supporting animals prone to muscle problems as well as supporting them in their recovery especially after an attack of azoturia which is also described as tying up, equine extertional rhabdomyolysis or Monday morning disease.

The invention also relates to the use of the composition of the fourth aspect of the invention for maintaining and improving of muscle health in an equine.

The invention also provides a method of maintaining and improving of muscle comprising administering, to an equine, a composition according to the fourth aspect of the invention.

The invention also provides a method of making a composition, according to the fourth aspect of the invention, comprising mixing together the ingredients into a composition e.g. in a tote tumbler to provide a powder, pellet composition or a paste.

According to a fifth aspect of the invention (also referred to as Challenged Joints), there is provided a composition comprising a source of glucosamine, a source of chondroitin sulphate, a source of sulphur (preferably an available source of sulphur), such as sulphur containing amino acids, or MSM (methysulphonylmethane), optionally glutamine (including a glutamine source), optionally a source of hyaluronic acid and one or more of boswellia, rosehips and a source of omega-3 fatty acids (preferably rich in DHA).

Sources of glucosamine include glucosamine hydrochloride, N-acetyl glucosamine, glucosamine sulphate. Sources of chondroitin sulphate include chicken cartilage, porcine cartilage, synthetic chondroitin sulphate. Sources of Hyaluronic acid include glucuronic acid. Sources of omega-3 fatty acids are described as above.

The composition is ideal for horses and ponies where joint health is a concern. It contains good levels of glucosamine, chondroitin sulphate, omega 3, optionally hyaluronic acid and a sulphur source, e.g. MSM, which are all known for their support of joint health. Hyaluronic acid helps to maintain joint lubrication and is an important component of cartilage. It may also contain: rosehips which are rich in natural antioxidants that may help support joint health; a vegetable source of omega 3 fatty acids preferably rich in DHA which may be lacking in the modern horse diet; boswellia, which has been used for its positive effects on join health; and optionally glutamine, which is important for the synthesis of proteoglycans (proteoglycans are found in connective tissue, cartilage and help lubricate the joint capsule). When joint health is less challenged during periods of reduced activity or stiffness, the composition described in the sixth aspect of the invention can be used for maintaining/supporting joint health.

Any one or more of the ingredients may be present in the following ranges (to provide the component of which they are a source): a source to provide glucosamine at 4-15 g, a source to provide chondroitin sulphate at 100-1000 mg, a bioavailable sulphur source (e.g. MSM at 4-15 g), a source to provide hyaluronic acid at 10-100 mg, a source to provide at glutamine at 50 mg to 5 g optionally at 50 µg-50 g, source to provide boswellia at 0.5-4 g, source to provide rosehip (shell, fruit or seeds) at 1-10 g, a source to provide omega-3 fatty acids (DHA) at 50-300 mg.

The composition may comprise glucosamine, MSM, chondroitin sulphate, optionally hyaluronic acid, optionally glutamine, boswellia, rosehips and omega-3 fatty acids.

The composition may comprise the following: glucosamine HCL about 7.5 g; chondroitin sulphate about 750 mg; MSM about 10 g; glutamine about 100 mg; hyaluronic acid about 50 mg; boswellia about 1 g; rosehips about 5 g; omega-3 fatty acids (e.g. DHA about 135 mg).

The composition may contain other ingredients which are used in an equine food, such as binders, flavorants (e.g. spearmint flavor, rosemary extract), or carriers such as calcium carbonate, wheat feed and/or rapeseed oil or others such as oils, pharmaceutically acceptable excipient, stabilizing agents, anticaking agents, emulsifiers. Spearmint flavor can be included in the range of 1-1000 mg, e.g. 100 mg. Rosemary extract, a natural antioxidant, can be included in the range of 5-100 mg (e.g. 25 mg). Calcium carbonate can be included at a range of from 50 mg-50 g (e.g. 12 g). Wheat feed can be included at a range from 100 mg-30 g (e.g. 254 mg). Rapeseed oil can be included at a range of form 150 mg-150 g (e.g. 250 mg) or milliliter equivalents.

The composition may be in the form of a food, such as a food supplement. The composition may be presented as a powder, crumb or solid form. A powder is useful to sprinkle on the main food of the equine animal. Other forms include solid pellets, granules, tablets or liquid.

The composition is recommended for feeding at the stated levels in a daily dose for a horse of 350-650 kg. A horse or pony of <350 kg would have a proportionally lower dose, adjusted accordingly. A horse of >650 kg would have a proportionally higher dose, adjusted accordingly.

The composition of the fifth aspect of the invention is particularly for use in maintaining and supporting joint health especially at periods of challenge, including easing stiffness (e.g. when ridden or when turned out) and supporting more comfortable movement, looseness, flexibility, freedom of movement and/or suppleness.

The invention also relates to the use of the composition of the fifth aspect of the invention for maintaining and supporting joint health in an equine as described in the paragraph immediately above.

The invention also relates to a method of maintaining and supporting joint health in an equine comprising administering, to an equine, a composition according to the fifth aspect of the invention as described in the two paragraphs immediately above.

The invention also provides a method of making a composition, according to the fifth aspect of the invention, comprising mixing together the ingredients into a composition, e.g. in a tote tumbler to produce a powder, pellet or a paste.

According to a sixth aspect of the invention (also referred to as Healthy Joints), there is provided a composition comprising a source of glucosamine, a source of chondroitin sulphate, a source of sulphur (preferably bioavailable sulphur, e.g. sulphur containing amino acids or MSM) and optionally glutamine.

The sources of glucosamine and chondroitin sulphate are as described above for the fifth aspect of the invention.

This composition is also ideal for horses and ponies to help maintain and support joint health in periods of less challenge or risk to joint health e.g. reduced activity or less stiffness (e.g. after a period of time with the fifth aspect of the invention). It includes glucosamine and chondroitin sulphate which are thought to be beneficial for cartilage structure and health. It contains a source of available (e.g. MSM) sulphur, which is essential for the synthesis of connective tissue, including collagen. It includes optionally glutamine which is important for the synthesis of proteoglycans. Proteoglycans are found in connective tissue, cartilage and help lubricate the joint capsule.

Any one or more of the ingredients may be present in the composition in the following ranges (to provide the component of which they are a source): a source to provide glucosamine HCL at 4-15 g; source to provide chondroitin sulphate at 100-1000 mg; source to provide MSM at 4-15 g; a source to provide glutamine at 50 mg-50 g optionally at 50 μg-50 g.

The composition may comprise glucosamine HCl, chondroitin sulphate, MSM and optionally glutamine.

The composition may comprise the following: a source to provide glucosamine HCl about 6.5 g; a source to provide chondroitin sulphate about 250 mg, a source of sulphur (e.g. MSM about 7.5 g); a source to provide glutamine about 100 mg.

The composition may contain other ingredients which are used in an equine food, such as binders, flavorants (e.g. spearmint flavor, rosemary extract), or carriers such as calcium carbonate, wheat feed and/or rapeseed oil or others such as oils, pharmaceutically acceptable excipient, stabilizing agents, anticaking agents, emulsifiers. Spearmint flavor can be included in the range of 1-1000 mg, e.g. 100 mg. Rosemary extract, a natural antioxidant, can be included in the range of 5-100 mg (e.g. 25 mg). Calcium carbonate can be included at a range of from 50 mg-50 g (e.g. 12 g). Wheat feed can be included at a range from 100 mg-30 g (e.g. 254 mg). Rapeseed oil can be included at a range of form 150 mg-150 g (e.g. 250 mg) or milliliter equivalents.

The composition may be in the form of a food, such as a food supplement. The composition may be presented as a powder, crumb or solid form. A powder is useful to sprinkle on the main food of the equine animal. Other forms include solid pellets, granules, tablets or a liquid.

The composition is recommended for feeding at the stated levels in a daily dose for a horse of 350-650 kg. A horse or pony of <350 kg would have a proportionally lower dose, adjusted accordingly. A horse of >650 kg would have a proportionally higher dose, adjusted accordingly.

The composition of the sixth aspect of the invention is particularly for use in maintaining or supporting joint health in an equine animal, such as those described according to the fifth aspect of the invention. The joint health may also be promoted.

The present invention also relates to a method of maintaining or supporting joint health in an equine, comprising administering, to an equine, a composition according to the sixth aspect of the invention.

The present invention also provides a method of making a composition, according to the sixth aspect of the invention, comprising mixing together the ingredients to form a composition e.g. in a tote tumbler to produce a powder, pellet or paste.

BRIEF DESCRIPTION OF THE DRAWINGS

The following specification may be better understood with reference to the attached Figures, wherein.

DETAILED DESCRIPTION

Figure 1:
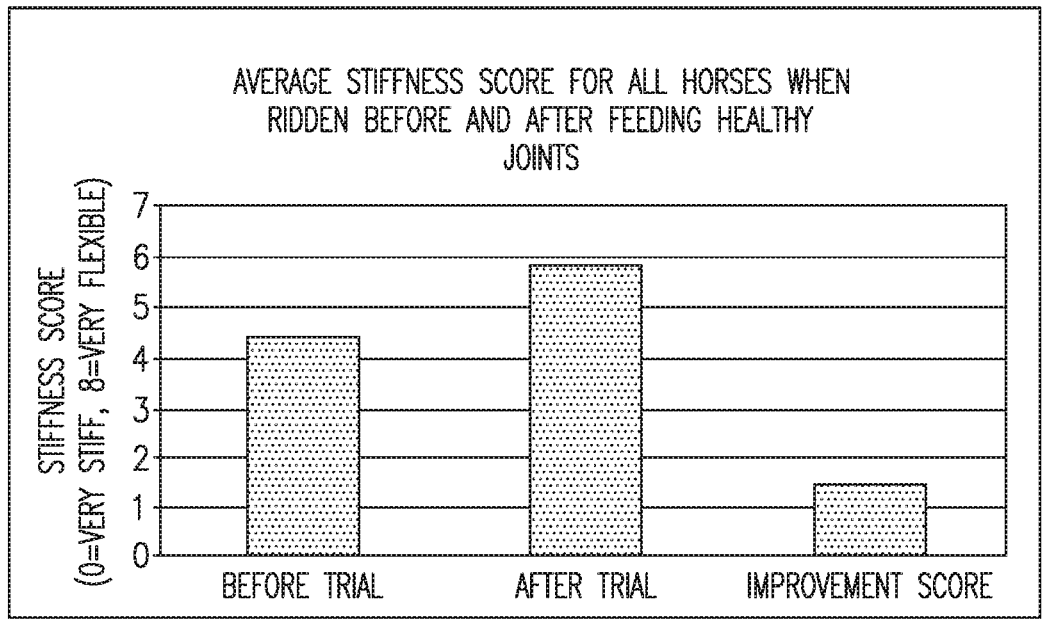
FIG. 1 is a graph depicting the results of a feeding trial conducted with an embodiment of the feed or supplement.

The composition of any of the aspects of the invention may be in the form of a food, in particular, in the form of a food supplement. The food supplement can additionally contain ingredients, which enable the food supplement to be formulated in a particular form. For example, the food supplement can contain molasses or molasses/oil mixture (including vegetable oil) for example cane molasses with approximately 6% or above oil such as Molglo (eg. to bind the ingredients together or as a palatability agent) or, oat feed, wheat feed or another suitable filler ingredient (as a filler ingredient). The food supplement may also contain a fiber source such as grasses, grass meal, alfalfa, sugar beet, soya hulls and oats, a fat source such as corn oil, soya oil, processed canola oil, coconut oil, palm oil or sunflower oil and/or a starch source such as cereals (e.g. corn or maize, barley, oats). Thus, the food supplement may be a food. The invention is described with reference to the following examples, which show the practical use of the aspects of the invention in day to day horse care and management.

EXAMPLES

The aim of the trials is to prove the product has benefits to the horse which are recognizable by its care giver and which relate to the product's intended use.

To ensure that the supplements are palatable to the horse. The following supplements were evaluated.

| Product Identifier | Functional Area | Specific Functional Area | Total Horses Required in Trial |
|---|---|---|---|
| 6th aspect of invention | Joint | Maintaining joint health | 20 Horses (already being fed or in the past been fed a competitor supplement) |

-continued

| Product Identifier | Functional Area | Specific Functional Area | Total Horses Required in Trial |
|---|---|---|---|
| 5th aspect of invention | Joint | Supporting Challenged Adult Joints | 20 Horses (cross-over)* (Horses not to have fed a competitor supplement) |
| 3rd aspect of invention | Behavior | Supporting Positive Behavior | 20 Horses (cross-over)* (Horses not to have fed a competitor supplement) |
| 1st aspect of invention | Behavior | Energy Boost For Laid Back Horses | 20 Horses (already being fed or in the past been fed a competitor supplement) |
| 2nd aspect of invention | Skin | Supporting Challenged Skin | 20 Horses (already being fed or in the past been fed a competitor supplement) |
| 4th aspect of invention | Performance | Supporting Challenged Muscles | 20 Horses (already being fed or in the past been fed a competitor supplement) |

Total horses recruited: 120
Cross-over trial
*Within the Joint and Behavior groups 20 horses were recruited from within each group who had an issue in the related area but were currently not feeding a competitor supplement. These 20 trialed our respective supplement for 5 weeks and a competitor supplement for 5 weeks with a 2 week wash out period in-between. Half the group feed the supplement to be tested first and the other half the competitor supplement first. Those who already feed a competitor supplement were recruited into the maintaining joint health functional area.

The competitor products are as follows:
Behavior (Competitor B)
Ingredients
Magnesium oxide, grass meal, hops, passion flower, calcium carbonate, white mineral oil, Brewers' yeast, magnesium chloride, fenugreek seed, oligofructose (dried), Saccharomyces cerevisiae extract.
Dose: 50-75 g loading dose and then 25-50 g maintenance dose. Dose is per day.
Joint (Competitor A)
Ingredients:
Dehydrated alfalfa meal, isolated soy protein, dextrose, avocado/soybean unsaponifiables (ASU), glycine, glutamine, chondroitin sulphate, glucuronic acid, proline, glutamic acid, hyaluronic acid, ammonium propionate (preservative), vegetable oil, monosilicic acid, aspartic acid, arginine, histidine, manganese sulphate, pyridoxine HCl (vitamin B6), ascorbic acid (Vitamin C), sulphur, alanine, serine, valine, isoleucine, copper sulphate 5 mg/kg (added).
Dose: 14 g loading dose and then 7 g maintenance dose. Dose is per day.
Additional Trial Aims Per Product (Care Giver Evaluated):

| Healthy Joints | Challenged Joints (Cross over trial) |
|---|---|
| Stiffness, when ridden Stiffness, when turned out | Stiffness when turned out, compared to competitor product Stiffness, when ridden, compared to competitor product |

| Calm Behavior (Positive Behavior) (Cross over trial) | Energy Boost |
|---|---|
| Spookiness/nervousness vs. competitor product Excitability/fizzy vs. competitor product | Energy/enthusiasm Focus/concentration |

| Challenged Skin and Coat | Challenged Muscles |
|---|---|
| Coat shine Coat scurf | Recovery rate after high intensity exercise Stiffness after high intensity exercise |

Trial Time Scale

| Functional Area | Product Identifier | Time Split | Total Time |
|---|---|---|---|
| Joint -Normal | 6th aspect | 12 wks | 12 weeks |
| Behavior - Normal | 1st aspect | 12 wks | 12 weeks |
| Skin | 2nd aspect | 12 wks | 12 wks |
| Performance | 4th aspect | 12 wks | 12 wks |

Cross over trials
Each horse was provided with enough supplement to last throughout the trial

| Functional Area | Product Identifier | Time Split | Total Time |
|---|---|---|---|
| Joint-CrossOver | 5th aspect | 5 wks-2 wks washout - 5 wks | 12 weeks |
| Behavior -Cross Over | 3rd aspect | 5 wks-2 wks washout - 5 wks | 12 weeks |

Figure 2:
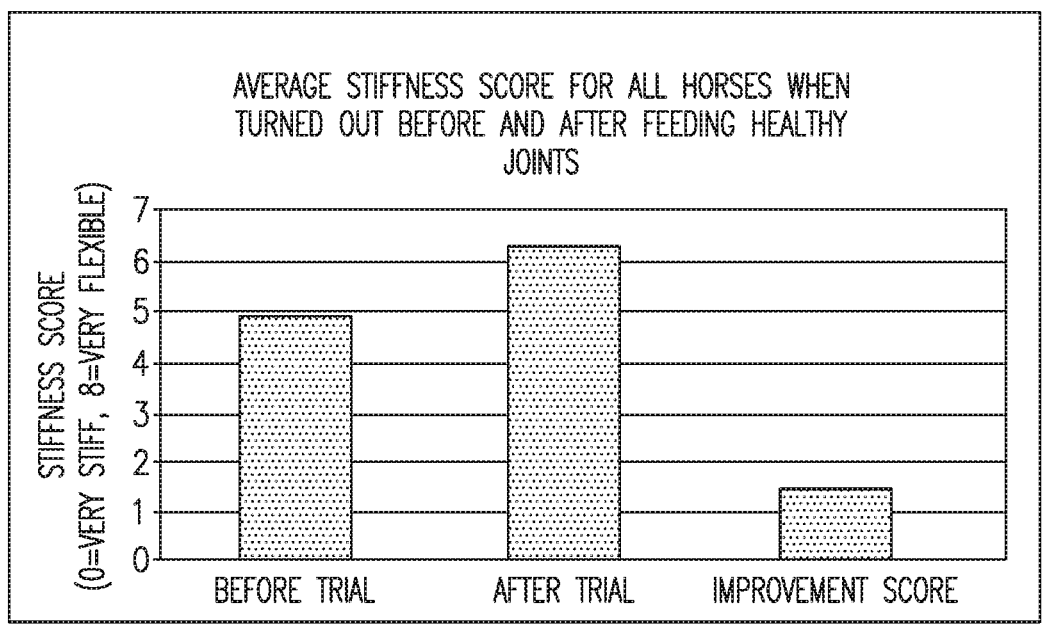
FIG. 2 is a graph depicting the results of a feeding trial conducted with an embodiment of the feed or supplement.
Figure 3:
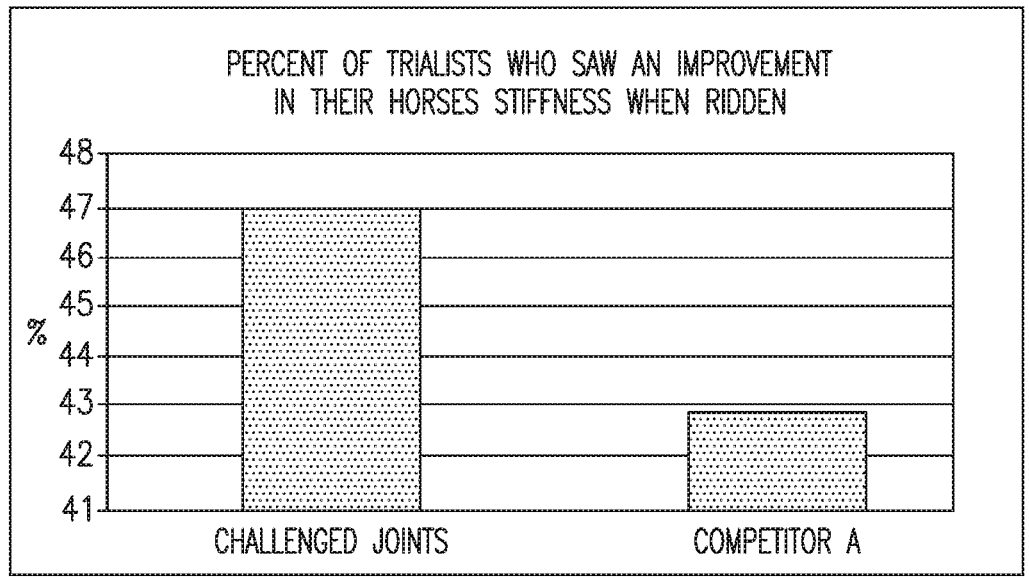
FIG. 3 is a graph depicting the results of a feeding trial conducted with an embodiment of the feed or supplement.

Data Collection and Analysis
Questionnaires were designed for the horse care giver to complete.
6th Aspect
Each horse care giver was asked to score each horse for stiffness, when ridden. The results are shown in FIG. 1.
Each horse care giver was asked to score each horse for stiffness, when turned out. The results are shown in FIG. 2.
In addition, the product was noted as palatable: 100% horses ate it. It was fast acting; 27% of care givers noticed a beneficial change within 1 week; 65% within 4 weeks. It was efficacious; see results graphs.
5th Aspect
Each horse care giver was asked to score the improvements in their horse stiffness when turned out. The results are shown in FIG. 3.

Figure 4:
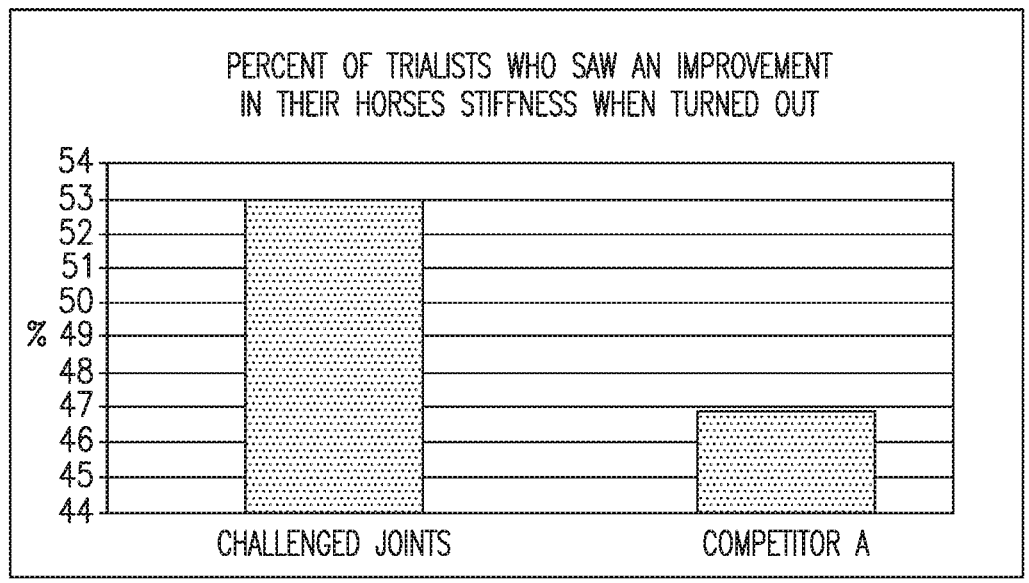
FIG. 4 is a graph depicting the results of a feeding trial conducted with an embodiment of the feed or supplement.

Each horse care giver was asked to score the improvement in stiffness when ridden. The results are shown in FIG. 4.

In addition, the product was noted as palatable. 87% horses ate it. It was fast acting; 48% of care givers noticed a beneficial change within 1 week; 72% within 4 weeks. It was efficacious; see results graphs.

1st Aspect

Figure 5:
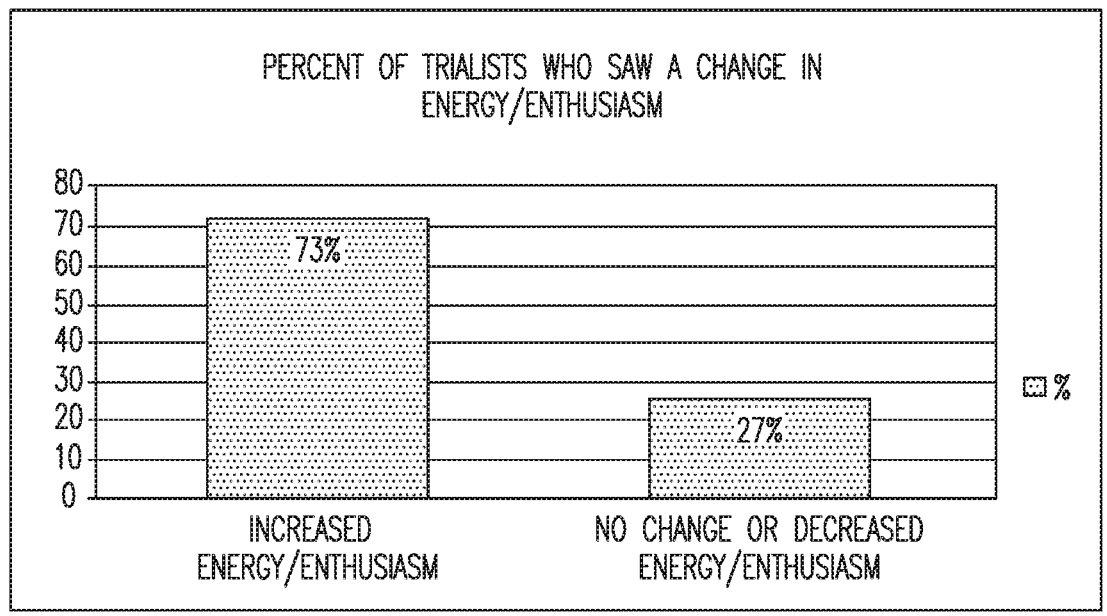
FIG. 5 is a graph depicting the results of a feeding trial conducted with an embodiment of the feed or supplement.

Each horse care giver was asked to score a change in energy/enthusiasm. The results are shown in FIG. 5.

Figure 6:
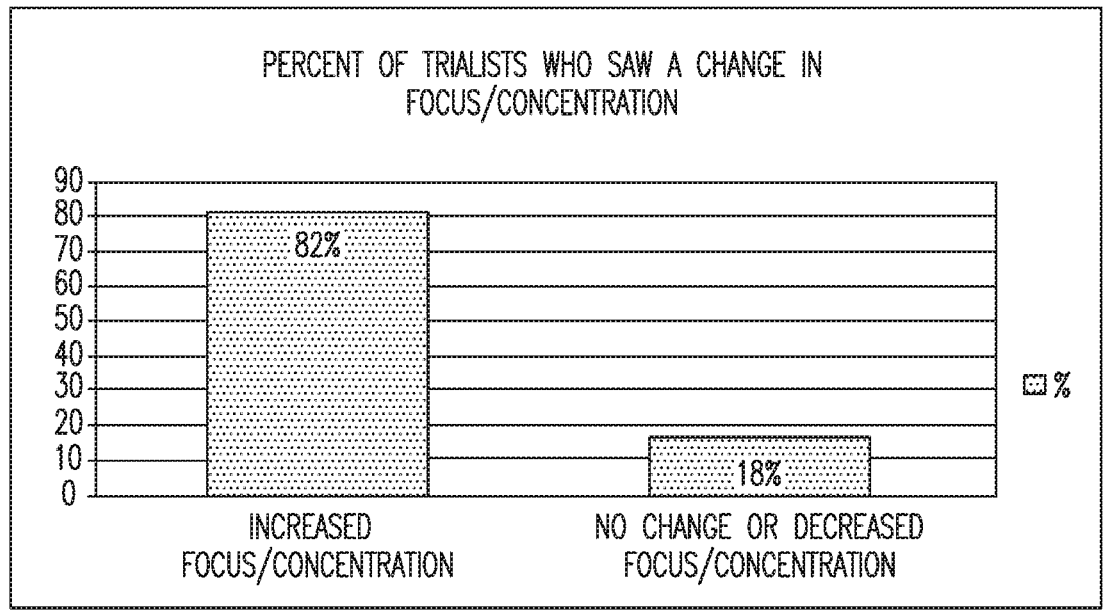
FIG. 6 is a graph depicting the results of a feeding trial conducted with an embodiment of the feed or supplement.

Each horse care giver was asked to score a change in focus/concentration. The results are shown in FIG. 6.

In addition, the product was noted as palatable. 91% horses ate it. It was fast acting; 36% of care givers noticed a beneficial change within 1 week; 68% within 4 weeks. It was efficacious; see results graphs.

3rd Aspect

Figure 7:
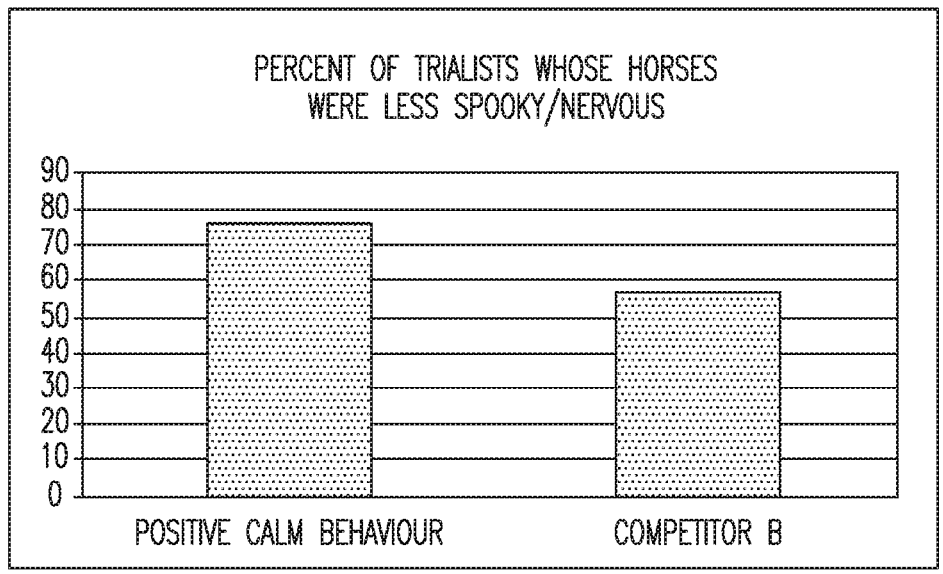
FIG. 7 is a graph depicting the results of a feeding trial conducted with an embodiment of the feed or supplement.

Each horse care giver was asked to score a change in the horse being spooky/nervous. The results are shown in FIG. 7.

Figure 8:
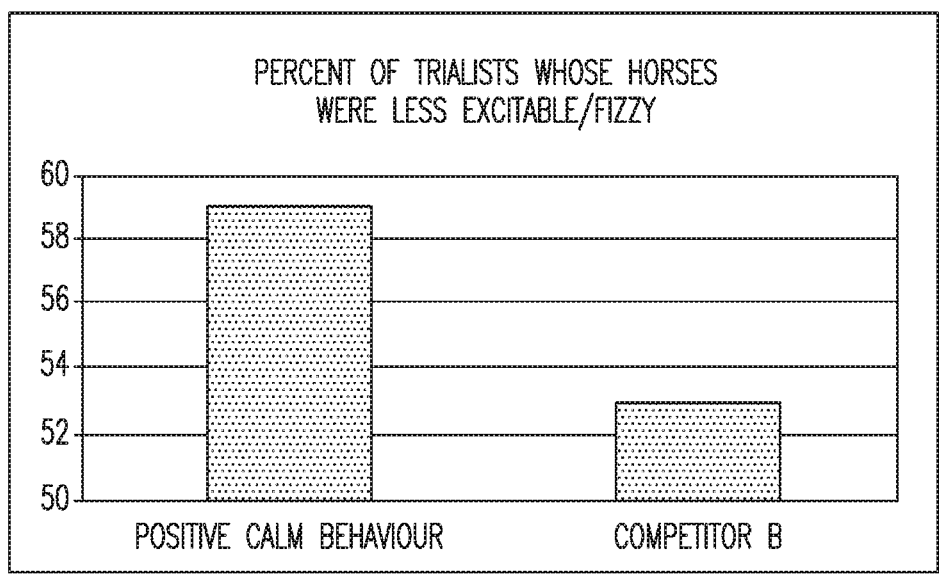
FIG. 8 is a graph depicting the results of a feeding trial conducted with an embodiment of the feed or supplement.

Each horse care giver was asked to score a change in the horse being excitable/fizzy. The results are shown in FIG. 8.

In addition, the product was noted as palatable. 94% horses ate it. It was fast acting; 65% of care givers noticed a beneficial change within 1 week; 76% within 4 weeks. It was efficacious; see results graphs.

2nd Aspect

Figure 9:
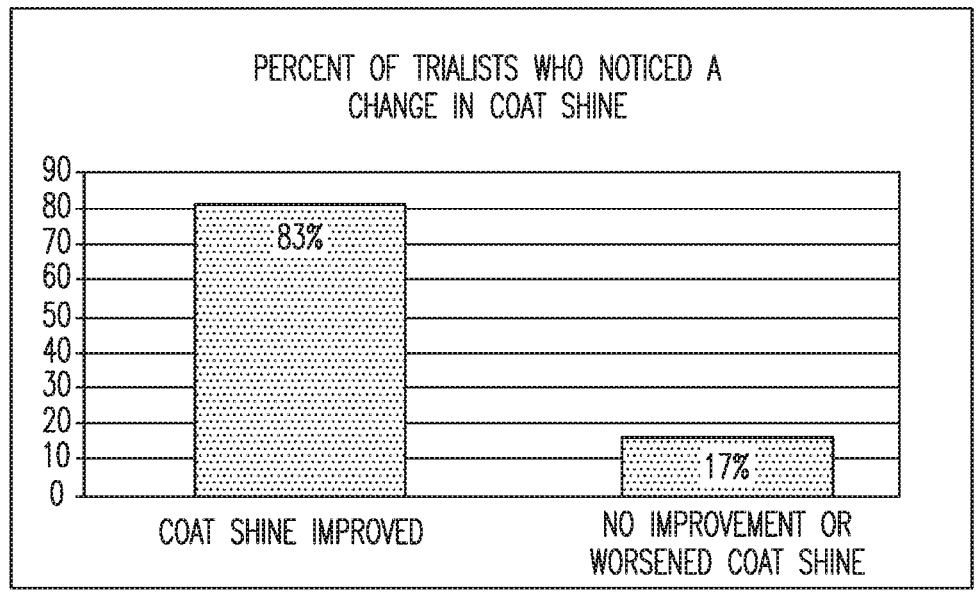
FIG. 9 is a graph depicting the results of a feeding trial conducted with an embodiment of the feed or supplement.

Each horse care giver was asked to score a change in coat shine. The results are shown in FIG. 9.

Figure 10:
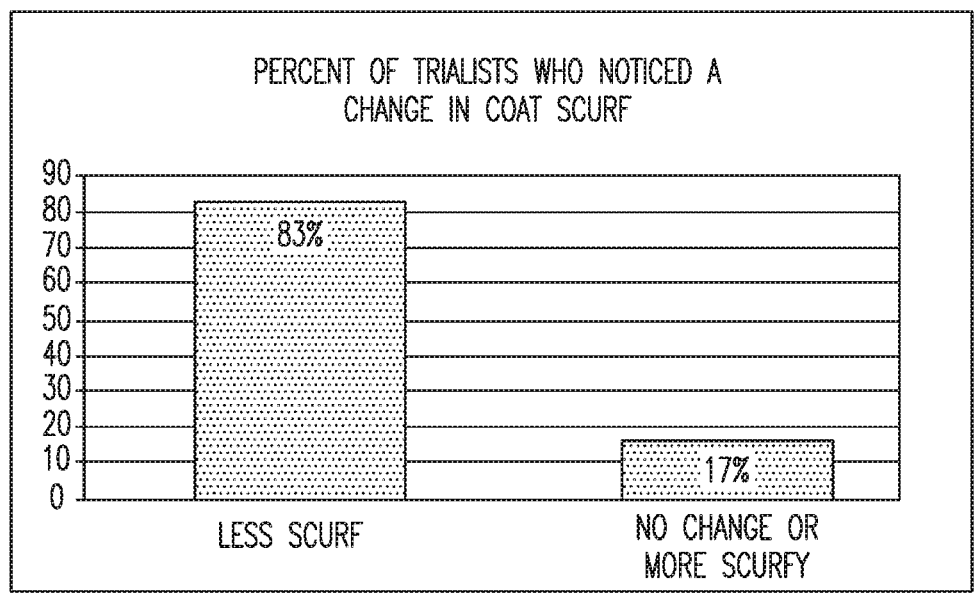
FIG. 10 is a graph depicting the results of a feeding trial conducted with an embodiment of the feed or supplement.

Each horse care giver was asked to score a change in coat scurf. The results are shown in FIG. 10.

In addition; it was palatable; 92% horses ate it. It was efficacious; see results graphs.

4th Aspect

Figure 11:
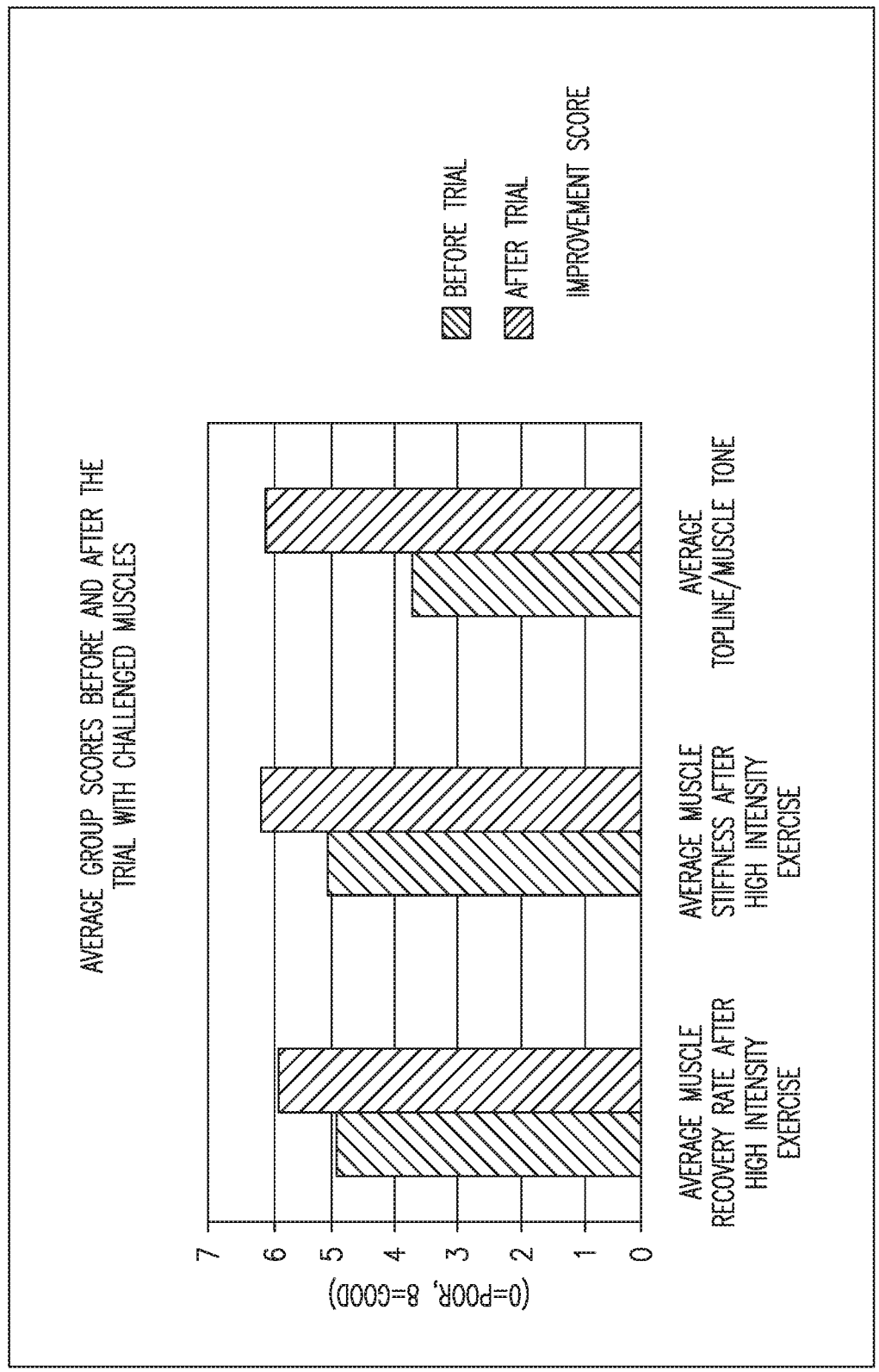
FIG. 11 is a graph depicting the results of a feeding trial conducted with an embodiment of the feed or supplement.

Each horse care giver was asked to score recovery rate after high intensity exercise, stiffness after high intensity exercise and topline/muscle tone, both before and after the trial. The results are shown in FIG. 11.

In addition; it was palatable; 95% horses ate it. It was fast acting; 24% of trialists noticed a beneficial change within 1 week; 68% within 4 weeks. It was efficacious; see results graph.

What is claimed is:

1. A equine feed or supplement consisting of:
   about 2 g to 15 g magnesium from one or more sources;
   about 2 g to 15 g of any species of chamomile;
   one or more of about 2 g to 15 g of any species of passion flower, about 2 g to 15 g of any species of lemon balm, or about 2 g to 15 g of any species of hops;
   optionally, one or more of thiamine, pyridoxine and folic acid, and/or yeast; and
   optionally, one or more binders, flavorants and/or carriers.

2. The equine feed or supplement of claim 1, wherein the source(s) of magnesium are selected from magnesium oxide, magnesium aspartate hydrochloride, magnesium carbonate or combinations of these.

3. The equine feed or supplement of claim 1, consisting of at least two sources of magnesium.

4. The equine feed or supplement of claim 1, optionally further consisting of about 50 mg-500 mg thiamine, about 50 mg-250 mg pyridoxine and about 2 mg to 100 mg folic acid and 2 g to 15 g yeast.

5. The equine feed or supplement of claim 4, consisting of about 6 g magnesium, 10 g chamomile, 5 g passion flower, 3 g lemon balm, 3 g hops, and optionally, 250 thiamine, 120 mg pyridoxine, 20 mg folic acid and/or 8 g yeast.

6. A method for promoting, supporting or maintaining calm behavior in an equine comprising administering to the equine an equine feed or supplement consisting of:
   about 2 g to 15 g of magnesium from one or more sources;
   about 2 g to 15 g of any species of chamomile;
   one or more of about 2 g to 15 g of any species of passion flower, about 2 g to 15 g of any species of lemon balm, or about 2 g to 15 g of any species of hops;
   optionally, one or more of thiamine, pyridoxine and folic acid, and/or yeast; and
   optionally, one or more binders, flavorants and/or carriers.

7. The method of claim 6, wherein the source(s) of magnesium is selected from magnesium oxide, magnesium aspartate hydrochloride, magnesium carbonate or combinations of these.

8. The method of claim 6, consisting of at least two sources of magnesium.

9. The method of claim 6, wherein the equine animal weighs from 350 kg to 650 kg and the feed or supplement optionally further consists of 50 mg-500 mg thiamine, about 50 mg-250 mg pyridoxine and about 2 mg to 100 mg folic acid and 2 g to 15 g yeast.

* * * * *